United States Patent [19]

Carlisle

[11] Patent Number: 5,439,603

[45] Date of Patent: Aug. 8, 1995

[54] LUBRICATING OIL ADDITIVES, THEIR PREPARATION AND USE

[75] Inventor: William D. Carlisle, Hull, England

[73] Assignee: BP Chemicals (Additives) Limited, London, England

[21] Appl. No.: 49,068

[22] Filed: Apr. 19, 1993

Related U.S. Application Data

[63] Continuation of Ser. No. 674,654, Mar. 25, 1991, abandoned.

[30] Foreign Application Priority Data

Mar. 31, 1990 [GB] United Kingdom ............. 9007335

[51] Int. Cl.$^6$ ............................................ C10M 133/56
[52] U.S. Cl. ........................ 252/51.5 A; 548/520; 548/546; 548/547
[58] Field of Search ............... 252/51.5 A; 548/520, 548/546, 547

[56] References Cited

U.S. PATENT DOCUMENTS

| | | | |
|---|---|---|---|
| 4,482,464 | 11/1984 | Karol et al. | 252/51.5 A |
| 4,617,137 | 10/1986 | Plavac | 252/51.5 A |
| 4,812,261 | 3/1989 | Liu et al. | 252/51.5 A |
| 4,834,776 | 5/1989 | Axelrod | 548/547 |
| 5,328,622 | 7/1994 | Emert et al. | 252/51.5 A |

FOREIGN PATENT DOCUMENTS 2008258 7/1990 Canada .
0183478 6/1986 European Pat. Off. .
1279081 11/1961 France .
1415006 9/1965 France .
1065595 4/1967 United Kingdom .

*Primary Examiner*—Ellen M. McAvoy
*Attorney, Agent, or Firm*—Brooks Haidt Haffner & Delahunty

[57] ABSTRACT

A lubricating oil soluble compound suitable for use as a dispersant additive is obtainable by reacting at elevated temperature an epoxyacrylate with a dispersant having at least one reactive nitrogen-containing moiety.

Intermediates of the general formula IV

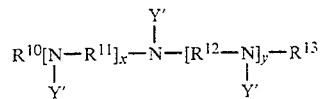

where Y' is a group derived from the reaction of the epoxyacrylate with reactive nitrogen-containing moieties (ie primary or secondary amines) are novel.

The process for preparing the lubricating oil soluble compounds can be a one step or multistep process.

Lubricating oil compositions comprise a major proportion of lubricating oil and a minor proportion of the lubricating oil soluble compounds.

11 Claims, No Drawings

LUBRICATING OIL ADDITIVES, THEIR PREPARATION AND USE

This application is a continuation of application Ser. No. 07/674,645, filed Mar. 25, 1991, now abandoned.

The present invention relates generally to novel lubricating oil soluble compounds suitable for use as dispersant additives in lubricating oils, their preparation and uses thereof.

Multigrade lubricating oils typically are characterised by two numbers such as 10W30, 5W30, and the like. The first number in the multigrade designation is associated with a maximum low temperature (e.g. −20° C.) viscosity requirement for that multigrade oil as measured typically by a cold cranking simulator (CCS) under high shear, while the second number in the multigrade designation is associated with a minimum high temperature (e.g. 100° C.) viscosity requirement. Thus, each particular multigrade oil must simultaneously meet both strict low and high temperature viscosity requirements in order to qualify for a given multigrade designation. Such requirements are set, for example, by ASTM specifications.

The minimum high temperature viscosity requirement is intended to prevent the oil from thinning out too much during engine operation thereby leading to excessive wear and increased oil consumption. The maximum low temperature viscosity requirement is intended to facilitate engine starting in cold weather and to ensure pumpability.

In formulating an oil which satisfactorily meets the extremes of viscosity requirements the formulator may use a single oil of desired viscosity or a blend of two lubricating oils of different viscosities at the same time as manipulating the nature and amounts of additives that must be present to achieve the overall target properties of a particular multigrade oil including its viscosity requirements.

In general, in order to meet the low and high temperature viscosity requirements of multigrade oils, it is necessary for the formulator to employ an additive conventionally referred to as a viscosity index (VI) improver. These generally function to increase the low temperature viscosity of the base oil to a lesser extent than they increase the high temperature viscosity. A complication for the formulator is the effect on the viscosity requirements posed by other lubricating oil additives, and in particular dispersants, which are added to prevent sludge flocculation and precipitation, the sludge being formed by oxidation of the oil. A problem with many existing dispersants is their low viscosities at higher temperatures.

The present invention seeks to overcome the problem associated with prior art dispersants by the provision of new lubricating oil soluble compounds suitable for use as dispersants having improved VI characteristics.

Accordingly, the present invention provides lubricating oil soluble compounds suitable for use as dispersant additives which pounds are obtainable by reacting at elevated temperature an epoxyacrylate with a dispersant having at least one reactive nitrogen-containing moiety.

Any dispersant having at least one reactive nitrogen containing moiety may be employed. Thus dispersants having primary and/or secondary amino groups may be employed but not those containing exclusively tertiary amino groups. It is believed, though we do not wish to be bound by any specific theory, that reaction occurs between the reactive nitrogen-containing moiety of the dispersant and both the epoxy and the olefinically unsaturated groups of the epoxyacrylate in a manner such that the dispersant is cross-linked by the epoxyacrylate molecules.

Suitable dispersants include (i) oil-soluble amides or imides of long chain hydrocarbyl-substituted mono- and dicarboxylic acids or their anhydrides, (ii) long chain hydrocarbons having a polyamine attached directly thereof, and (iii) Mannich condensation products formed by condensing a long chain hydrocarbyl-substituted hydroxy aromatic compound, for example an alkyl phenol, with an aldehyde and a polyalkene polyamine, which adduct contains at least one reactive amino group.

The dispersant is preferably an imide or amide formed by the reaction of a polyalkene substituted succinic acylating agent and an amine. Succinimides are a well-known class of dispersant useful in the process of the present invention. Typical of the art relating to such materials is GB-A-1565627 and the prior art acknowledged therein. Typically, they are prepared by reacting a polyalkene, in the presence or absence of chlorine, with either maleic acid, or preferably maleic anhydride, to produce a polyalkene-substituted succinic acid or anhydride and thereafter reacting the polyalkene-substituted succinic acid or anhydride with a nitrogenous material, suitably an amine, which may be a mono-, di- or polyamine.

A suitable succinimide has the formula:

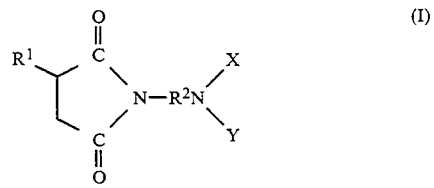

(I)

wherein $R^1$ is a hydrocarbyl group typically a polyolefin group, $R^1$ preferably contains between 30 and 300 carbon atoms more preferably between 50 and 150. $R^2$ is a divalent group such that $H_2NR^2NXY$ is an alkylene amine, such as an ethylene or propylene amine, e.g. $R^2$ is $-(CH_2CH_2NH)_kCH_2CH_2-$ where k is zero or an integer from 1 to 7 preferably 2 to 6, alternatively a mixed ethylene/propylene amine e.g. $H_2N(CH_2)_3NH(CH_2)_2NH(CH_2)_3NH_2$ can be used, X and Y are independently either hydrogen, alkyl preferably $C_{1-6}$ more preferably methyl or ethyl or hydroxy alkyl preferably $C_1-C_6$, most preferably hydroxy-ethyl, or together form the group:

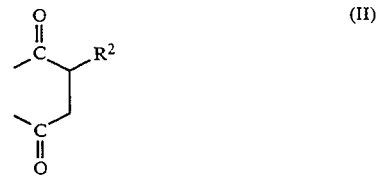

(II)

Alternatively, $R^2$ in the formula (I) may be a divalent group such that $H_2NR^2NXY$ is an alkanolamine or a polyether amine. Typically such alkanolamines may contain the group $=N.CH_2CH_2NH.CH_2CH_2OH$ (i.e. $R^2=CH_2CH_2$, $X=H$, $Y=CH_2CH_2OH$) and typically such polyether amines may contain the group $=N.CH_2CH_2O$ $CH_2CH_2OCH_2CH_2NH_2$ (i.e. $R^2=(CH_2CH_2O)_2CH_2CH_2-$, $X=Y=H$). Useful commercially available polyether amines are the Jeffamines (RTM) marketed by Texaco. $R^2$ is preferably an alkylene group e.g. of 2 to 40 carbons, optionally interrupted with at least one O or NH group, and in particular contains one or more units of alkylene oxa or alkylene amino groups each of 2 to 4 carbons.

$R^2$ may also be a divalent group such that $H_2NR^2NXY$ is an aromatic or araliphatic amine e.g. of 6-20 carbons such as phenylene or biphenylene diamine or bis(amino benzyl).

Where one of X and Y is hydrogen, $R^2$ may be an alkylene group e.g. $-CH_2CH_2-$. It is preferred that the dispersant used in the present invention contains at least 2 preferably from 3 to 7 active nitrogens (i.e. primary or secondary).

Suitably in the formulae (I) and (II) $R^1$ is derived from either ethylene, propylene, 1-butone, isobutene, 1-hexene, 1-octene and the like. Alternatively, the polyalkene may be derived from an internal olefin, e.g. 2-butene, or an interpolymer, e.g. an ethylene/propylene copolymer. Preferably the polyalkene is a polyisobutene.

The succinimide may be either a mono- or bis-succinimide.

For the purposes of the present invention, an epoxyacrylate is defined as a compound comprising at least one oxirane ring and at least one acrylate or acrylamide group, including alpha substituted derivatives of acrylate and acrylamide groups.

Epoxyacrylates useful in the present invention may suitably be those having the formula:

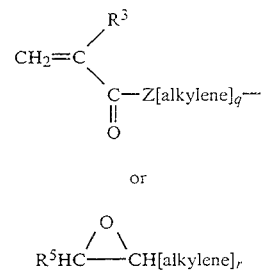

(III)

wherein $R^3$ and $R^5$ are independently either hydrogen, a hydrocarbyl or a hetero- (e.g. O) substituted hydrocarbyl group $R^4$ is alkylene, alkylene glycol, arylene or a group containing at least one of a acrylate acrylamide or oxirane group e.g. alkylene acrylate (or its amine derivative). Preferably $R^3$ is either hydrogen or a hydrocarbyl group e.g. of 1-20 carbons. Suitably the hydrocarbyl group may be either alkyl, cycloalkyl, aryl or alkaryl, preferably alkyl e.g. of 1-6 carbons. Z is a heteroatom, or a substituted heteroatom for example $-O-$ or $=NR^6$ where $R^6$ is hydrogen or an alkyl group e.g. of 1-6 carbons such as methyl or ethyl.

In formula III, where $R^4$ is alkylene e.g. of 1-300 or 1-10 carbons, it is suitably of the formula $-[CHR^7]_n-$ where $R^7$ is hydrogen or a $C_1-C_{20}$ preferably $C_1-C_6$, more preferably methyl or ethyl; n is an integer from 1 to 30; each of the n groups $R^7$ can be the same or different. The group $R^4$ is suitably derived from a polyolefin for example where $R^7$ is hydrogen, $R^4$ will typically be derived from polyethylene. $R^4$ is preferably $-CH_2-$.

Where $R^4$ is an alkylene glycol, it is suitably of the formula $-[CHR^8CHR^9O]_mCHR^8CHR^9-$ where $R^8$ and $R^9$ are independently hydrogen, or a $C_1-C_{25}$ preferably $C_1-C_{16}$ more preferably $C_1-C_6$ alkyl group for example methyl or ethyl, m is an integer from 1 to 10. Preferably $R^8$ is hydrogen and $R^9$ is hydrogen, methyl or ethyl. Where $R^9$ is hydrogen, methyl or ethyl, the alkylene glycol will usually be derived from ethylene propylene or butylene oxides respectively. Each of the $[CHR^8CHR^9O]$ groups can be the same of different.

$R_4$ may also be an arylene, alkarylene or aralkylene group e.g. of 6-20 or 7-20 carbons such as phenylene $-C_6H_4-$; benzylene $-CH_2C_6H_4-$; biphenylene $-C_6H_4-C_6H_4-$; methylene diphenylene $-C_6H_4CH_2C_6H_4-$ naphthylene $-C_{10}H_8-$ or $-C_6H_4C(CH_3)_2-C_6H_4-$.

Alternatively $R_4$ may comprise at least one acrylate, acrylamide or oxirane group e.g. $R_4=-[CAB]_p-$ where each of A and B is independently the group

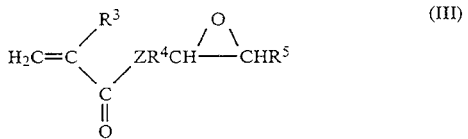

or $$R^5HC\underset{O}{\overset{}{\diagup\hspace{-0.5em}\diagdown}}CH[alkylene]_r$$

p is an integer from 1 to 10, e.g. 3–5 q and r are independently zero or an integer from 1 to 5 (this group preferably representing group A in at least one part of $R^4$) or is hydrogen, $R^7$, a hydroxy alkyl, each of the p groups $-[CAB]-$ may be the same or different, $R^3$, Z, $R^5$ and $R^7$ are all as defined above, and each alkylene group preferably has 1–6 carbons.

Preferably alkylene in the group A is methylene. When B is a hydroxy alkyl group it is preferably hydroxy ethyl.

$R^4$ is preferably an alkylene or an alkylene glycol, especially in the form $-CHR^7CABCHR^7-$.

Where $R^3$ or $R^5$ is a hydrocarbyl group it is preferably a $C_1-C_6$ alkyl group.

$R^3$ and $R^3$ are preferably hydrogen or methyl.

An example of a suitable epoxyacrylate having the formula III is glycidylacrylate. The dispersant having the formula (II) may be reacted with the epoxyacrylate having the formula (III) in a single step or in two or more sequential steps. Thus, the reaction of the dispersant with the epoxyacrylate may suitably comprise in a first step reacting dispersant at elevated temperature with epoxyacrylate, and in a further step or steps reacting the product from the preceding step or steps with further dispersant.

It will be appreciated that in the subsequent sequential step or steps involving the addition of further dispersant, a different dispersant or dispersants to that used in the first step may be employed.

It is preferred to effect the reaction in a suitable solvent. In view of the fact that dispersants are generally marketed as solutions in lubricating oils and in view of the intended use of the product, it is preferred to employ a lubricating oil as the solvent. Both natural and synthetic lubricating oils may be employed. Cosolvents may also be used if desired. Suitable cosolvents include liquid hydrocarbons, for example xylene and toluene.

The elevated temperature at which the reaction is effected may be above 70° C. and below the decomposition temperature of any of the components of the reaction mixture.

A single step process may suitably comprise adding over a period, for example over a period of from 5 to 180 minutes, the epoxyacrylate to a solution of the dispersant at a temperature of from 75° to 220° C. and thereafter reacting the mixture at a temperature above 70° C. and below the decomposition temperature of the mixture for a period sufficient to effect reaction, for example from 30 to 300 minutes, at either atmospheric or subatmospheric pressure. The epoxyacrylate may suitably be pre-heated if desired to a temperature below its decomposition temperature.

A two step process may suitably comprise (i) mixing the dispersant and the epoxyacrylate at a temperature of from ambient to 120° C. (ii) in the event that the temperature of the mixture is less than 70° C., raising its temperature to a value above 70° C. and below the decomposition temperature of the mixture over a period, for example from 10 to 180 minutes, (iii) maintaining the mixture at this temperature for a period, for example from 15 to 300 minutes, (iv) adding a further portion of a dispersant, suitably preheated to a temperature up to 220° C., and (v) maintaining the temperature of the mixture at a value in the range from 70° to 250° C. for a period, suitably from 15 to 300 minutes, at either atmospheric or subatmospheric pressure.

In the one step process at least 1 equivalents e.g. 1–10 equivalents of NH group in the dispersant may be reacted per equivalent of epoxyacrylate.

In the aforesaid two step (or multistep) reaction 0.75 or more, preferably from 0.85 to 1.1 equivalents of epoxyacrylate may be used in the first step for each amino hydrogen present in the dispersant. Thereafter in the subsequent stepp or steps, from 0.5–15, preferably 1–10 equivalents of dispersant per equivalent of dispersant used in the first step may be used.

The process may be operated batchwise or continuously.

Products of the first step of a 2-step or multistep reaction of a dispersant as described hereinabove and a polyacrylate of formula III comprise a novel compound of the general formula IV:

$$R^{10}[N-R^{11}]_x-N-[R^{12}-N]_y-R^{13}$$
$$\underset{Y^1}{|} \quad \underset{Y^1}{|} \quad \underset{Y^1}{|}$$

IV where $R^{11}$ and $R^{12}$ are independently a divalent aliphatic, hetero-substituted aliphatic, aromatic or hetero-substituted aromatic group, e.g. as defined for $R^2$ and with any aromatic groups containing 6–20 carbons such as phenylene.

$R^{10}$ and $R^{13}$ are independently a hydrocarbyl group, or

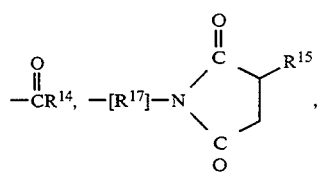

-continued

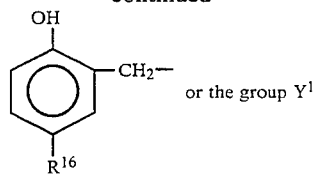

or the group $Y^1$ $Y^1$ is

or $H_2C=CR^3(CO)ZR^4CHR'CHR''R^5-$ where one or R' and R" is hydrogen and the other is hydroxyl. $R^{14}$ $R^{15}$ and $R^{16}$ are independently a hydrocarbyl group $R^{17}$ is a divalent aliphatic or hetero (e.g. 0) substituted aliphatic group, e.g. as defined for $R^2$.

x and y are independently zero or an integer from 1 to 10.

each group $R^{11}$ each $R^{12}$ and each group $Y^1$ can be the same or different, $R^3$, $R^5$, $R^6$, Z are as defined above.

Where $R^{10}$, $R^{13}$, $R^{14}$, $R^{15}$ or $R^{16}$ is a hydrocarbyl group e.g. of 1–300 carbons it is preferably derived from a polyolefin which is derived from a $C_1$-$C_8$ terminal or internal olefin e.g. polyethylene, polypropylene or polyisobutene preferably polyisobutene. Preferably it is a $C_{30}$-$C_{300}$ alkyl group more preferably $C_{50}$-$C_{150}$.

$R^{17}$ is suitably ethylene or propylene.

The reactions are performed in the absence of any catalystwhich is active in the polymerisation of epoxyacrylates. By the avoidance of such catalysts the production of polymerised epoxyacrylates can be substantially avoided.

In another aspect the present invention provides a finished lubricating oil composition which composition comprises a major proportion of a lubricating oil and a minor proportion of the dispersant additive of the invention or a compound of general formula IV as hereinbefore described.

The lubricating oil may be any natural or synthetic lubricating oil.

Into the lubricating oil composition there may also be incorporated any of the conventional additives normally employed, which additives include antioxidants, detergents, extreme pressure/anti-wear agents and viscosity index improvers. It is an advantage of the present invention that, because the dispersant composition of the invention has viscosity index properties, less of the conventional viscosity index improver may be required.

The lubricating oil composition may be used for any lubricating application, including automotive and marine use.

For automotive use the lubricating oil composition may suitably contain up to 10% (e.g. 0.01–10% or 2–10%) by weight of the dispersant additive of the present invention.

For marine engine use the lubricating oil composition may suitably contain up to 10% (e.g. 0.01–10% or 2–10%) by weight of the dispersant additive of the present invention.

The invention will now be illustrated by reference to the following Examples.

In all the Examples there was used a commercially available succinimide dispersant formed by the reaction of a polyisobutene ($M_n$ about 1000)—substituted succinic anhydride and tetraethylene pentamine.

In the Table reference is made to LZ 6420, which is a dispersant having VI credit marketed by Lubrizol. It is used for comparison purposes.

EXAMPLE

The succinimide dispersant was combined with four equivalents of glycidylacrylate at 20° C. The mixture was heated to 110° C. over 35 minutes and maintained at this temperature for 35 minutes. A further two equivalents of the succinimide dispersant at a temperature of 75° C. were added to the mixture. The mixture was heated at 120° C. for 240 minutes at atmospheric pressure and for 90 minutes at reduced pressure (60 mm Hg).

The viscosities of 11.0% b.w. lubricating oil solutions of the product were determined at $-20°$ C., 40° C. and 100° C. The measured values are presented in the accompanying Table.

TABLE

| | Concn. of product** (% b.w.) | Concn. of actives* (% b.w.) | VISCOSITY $-20°$ C. c/s | 40° C. c/s | 100° C. c/s | VI |
|---|---|---|---|---|---|---|
| LZ6420 | — | 5.5 | 38.00 | 53.2 | 8.38 | 131 |
| Succinimide | 11.0 | 5.5 | 35.75 | 43.2 | 6.76 | 108 |
| Succinimide:GA: Succinimide | 11.0 | 5.9 | 32.3 | 43.2 | 7.32 | 132 |
| 1:4:2 | 13.0 | 7.0 | — | 45.1 | 7.74 | 139 |

*'Actives' refers to any material that is not mineral oil, ie amount of succinimide + epoxyacrylate derived products present by weight.
**'Concn of product' refers to % weight of end material (which contains oil already) diluted in oil.

I claim:

1. A lubricating oil soluble compound suitable for use as a dispersant additive which compound is obtainable by reacting at a temperature above ambient and below the decomposition temperature of any of the components of the reaction mixture a dispersant having at least one reactive nitrogen-containing moiety selected from the group consisting of (i) succinimides of the formula (I):

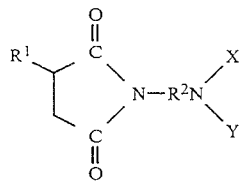

wherein $R^1$ is a polyalkene group having more than 30 carbon atoms and $R^2$ is a divalent group derived such that $H_2NR^2NXY$ is alkylene amine, an alkanolamine, a polyetheramine or an aromatic or araliphatic amine, and X and Y are independently hydrogen, an alkyl group or a hydroxyalkyl group or together form a group:

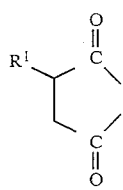

and (ii) long chain hydrocarbons having a polyamine attached directly thereto, with an epoxyacrylate having the formula (III):

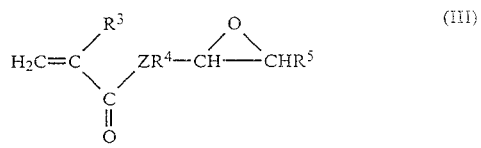

wherein $R^3$ and $R^5$ are independently either hydrogen, a hydrocarbyl or a hetero-substituted hydrocarbyl group, $R^4$ is a alkylene, alkylene glycol, aryl or a group containing at least one of an acrylate, acrylamide or oxirane group, and Z is oxygen or $=NR^6$ where $R^6$ is hydrogen or an alkyl group, the dispersant being reacted with epoxyacrylate having the formula (III) in two or more sequential steps, in a first step reacting the dispersant with the epoxyacrylate using at least 0.75 equivalents of the epoxyacrylate for each amino hydrogen present in the dispersant, and in a subsequent step, or steps, reacting the product from the preceding step with further dispersant using from 0.5 to 15 equivalents of dispersant per equivalent of dispersant used in the first step.

2. An oil-soluble compound as claimed in claim 1 wherein $R^1$ is a polyisobutene group.

3. An oil-soluble compound as claimed in claim 1 wherein the group $R^2$ is a divalent group of the formula:

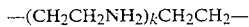
—(CH$_2$CH$_2$NH$_2$)$_k$CH$_2$CH$_2$— where k is an integer from 2 to 6.

4. An oil-soluble compound as claimed in claim 1 wherein the dispersant contains between 3 and 7 active nitrogens.

5. An oil-soluble compound as claimed in claim 1 wherein $R^4$ is an alkylene group of formula —[CHR$^7$]$_n$— where $R^7$ is hydrogen or a $C_1$-$C_6$ alkyl group, and each of the n—[CHR$^7$]— groups can be the same or different.

6. An oil-soluble compound as claimed in claim 1 wherein $R^4$ is an alkylene glycol of the formula:

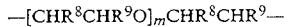
—[CHR$^8$CHR$^9$O]$_m$CHR$^8$CHR$^9$— where $R^8$ and $R^9$ are independently hydrogen or a $C_1$-$C_6$ alkyl group and m is an integer from 1 to 10.

7. An oil-soluble compound as claimed in claim 1 wherein $R^4$ is a group containing at least one of an acrylate, acrylamide or oxirane group of the formula

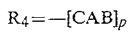
$R_4$=—[CAB]$_p$ where each of A and B is independently the group

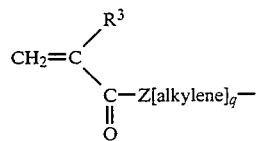

or

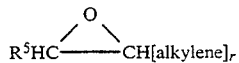

p is an integer from 1 to 10, q and r are independently zero or an integer from 1 to 5, or is hydrogen, $R^7$, a hydroxy alkyl, each of the p groups —[CAB]— may be the same or different, $R^3$ and $R^5$ are independently either hydrogen, a hydrocarbyl or a hetero-substituted hydrocarbyl group, Z is a heteroatom or substituted heteroatom, and $R^7$ is hydrogen or an alkyl group containing from 1 to 6 carbon atoms.

8. An oil-soluble compound as claimed in claim 1 wherein $R^3$ and $R^5$ are independently hydrogen or methyl.

9. A lubricating oil composition comprising a major proportion of a lubricating oil and a minor proportion of an oil-soluble compound as claimed in claim 1.

10. A process for preparing a lubricant oil soluble compound suitable for use as a dispersant additive which comprises reacting at a temperature above ambient and below the decomposition temperature of any of the components of the comprises reacting at a temperature above ambient and below the decomposition temperature of any of the components of the reaction mixture a dispersant having at least one reactive nitrogen-containing moiety selected from the group consisting of (i) succinimides of the formula (I):

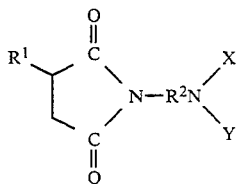

wherein $R^1$ is a polyalkene group having more than 30 carbon atoms and $R^2$ is a divalent group derived such that $H_2NR^2NXY$ is alkylene amine, an alkanolamine, a polyetheramine or an aromatic or araliphatic amine, and X and Y are independently hydrogen, an alkyl group or a hydroxyalkyl group or together form a group:

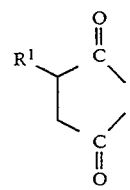

and (ii) long chain hydrocarbons having a polyamine attached directly thereto, with an epoxyacrylate having the formula (III):

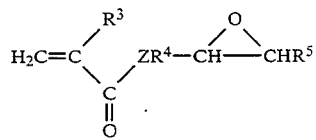

wherein $R^3$ and $R^5$ are independently either hydrogen, a hydrocarbyl or a hetero-substituted hydrocarbyl group, $R^4$ is a alkylene, alkylene glycol, aryl or a group containing at least one of an acrylate, acrylamide or oxirane group and Z is oxygen or $=NR^6$ where $R^6$ is hydrogen or an alkyl group, the dispersant being reacted with epoxyacrylate having the formula (III) in two or more sequential steps, in a first step reacting the dispersant with epoxyacrylate using at least 0.75 equivalents of the epoxyacrylate for each amino hydrogen present in the dispersant, and in a subsequent step, or steps, reacting the product from the preceding step with further dispersant using from 0.5 to 15 equivalents of dispersant per equivalent of dispersant used in the first step.

11. A process as claimed in claim 10 wherein the epoxyacrylate is used in the first step in an amount in the range 0.85 to 1.1 equivalents of epoxyacrylate to amino hydrogen present in the dispersant used in the first step.

* * * * *

UNITED STATES PATENT AND TRADEMARK OFFICE
CERTIFICATE OF CORRECTION

PATENT NO. : 5,439,603
DATED : August 8, 1995
INVENTOR(S) : WILLIAM D. CARLISLE

It is certified that error appears in the above-indentified patent and that said Letters Patent is hereby corrected as shown below:

Col. 2, lines 55-63, in formula II, change "$R^2$" to --$R^1$--

Col. 3, line 20, change "1-butone" to --1-but$\underline{e}$ne--

Col. 4, line 41, second occurrence, change "$R^3$" to --$R^5$--

Col. 4, line 52, change "it" to --It--

Signed and Sealed this

Fifth Day of March, 1996

Attest:

BRUCE LEHMAN

Attesting Officer        Commissioner of Patents and Trademarks